US008017652B2

(12) United States Patent
Shidoji et al.

(10) Patent No.: US 8,017,652 B2
(45) Date of Patent: *Sep. 13, 2011

(54) ACTIVATORS OF PEROXISOME PROLIFERATOR-ACTIVATED RECEPTORS

(75) Inventors: Yoshihiro Shidoji, Nagasaki (JP); Naoto Ishibashi, Saitama (JP)

(73) Assignees: Kowa Company Ltd., Aichi (JP); Nagasaki Prefectural and Municipal Universities Corporation, Nagasaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,197

(22) Filed: May 8, 2009

(65) Prior Publication Data

US 2009/0264529 A1  Oct. 22, 2009

Related U.S. Application Data

(60) Continuation of application No. 11/845,684, filed on Aug. 27, 2007, now Pat. No. 7,547,730, which is a division of application No. 11/272,864, filed on Nov. 15, 2005, now abandoned, which is a continuation of application No. 10/257,391, filed as application No. PCT/JP01/03442 on Apr. 23, 2001, now abandoned.

(30) Foreign Application Priority Data

Apr. 24, 2000  (JP) ................................. 2000-122974

(51) Int. Cl.
*A61K 31/20* (2006.01)

(52) U.S. Cl. ....................................... 514/560; 514/866

(58) Field of Classification Search .................. 514/560, 514/866
See application file for complete search history.

(56) References Cited

U.S. PATENT DOCUMENTS

| | | |
|---|---|---|
| 4,346,109 A | 8/1982 | Yamatsu et al. |
| 4,491,592 A | 1/1985 | Katoh et al. |
| 4,655,973 A | 4/1987 | Yamatsu et al. |
| 4,757,140 A | 7/1988 | DeLuca et al. |
| 4,788,330 A | 11/1988 | Nakamoto et al. |
| 4,841,038 A | 6/1989 | DeLuca et al. |
| 4,883,916 A | 11/1989 | Nakamoto et al. |
| 4,888,439 A | 12/1989 | Yamatsu et al. |
| 4,917,829 A | 4/1990 | Yamatsu et al. |
| 4,988,732 A | 1/1991 | Yamatsu et al. |
| 5,852,057 A | 12/1998 | Muto et al. |
| 6,369,251 B1 | 4/2002 | Takano et al. |
| 6,984,742 B2 | 1/2006 | Tanikawa et al. |
| 7,547,730 B2 * | 6/2009 | Shidoji et al. ............ 514/560 |
| 2005/0250671 A1 | 11/2005 | Shidoji et al. |
| 2006/0094784 A1 | 5/2006 | Kagawa et al. |

FOREIGN PATENT DOCUMENTS

| | | |
|---|---|---|
| DE | 781809 | 8/1957 |
| EP | 054732 | 6/1982 |
| EP | 0107188 | 5/1984 |
| EP | 194693 | 9/1986 |
| EP | 0847754 | 6/1998 |
| EP | 1046630 | 3/2003 |
| GB | 2073750 | 10/1981 |
| JP | 54-046821 | 4/1979 |
| JP | 55-22645 | 2/1980 |
| JP | 55-138457 | 10/1980 |
| JP | 58-109415 | 6/1983 |
| JP | 61-210050 | 9/1986 |
| JP | 62-77317 | 4/1987 |
| JP | 63-32058 | 6/1988 |
| JP | 6332058 | 6/1988 |
| JP | 63-166824 | 7/1988 |
| JP | 6334855 | 7/1988 |
| JP | 10-167960 | 6/1998 |
| JP | 11-511472 | 10/1999 |
| JP | 2000122974 | 4/2000 |
| WO | 94/22818 | 10/1994 |
| WO | 97/10819 A1 | 3/1997 |
| WO | 01/15702 | 3/2001 |
| WO | 01-80854 | 11/2001 |
| WO | 03/097034 | 11/2003 |
| WO | 2004/017958 | 3/2004 |

OTHER PUBLICATIONS

U.S. Appl. No. 10/524,420, to Reiko Kawamura et al., filed Aug. 19, 2003.
Nariaki Nakamura et al., "Apoptosis in Human Hepatoma Cell Line Induced by 4,5-Didehydrogeranylgeranoic Acid (Acyclic Retinoid) Via Down-Regulation of Transforming Growth Factor-α," Biochemical and Biophysical Research Communications, vol. 219, No. 1, pp. 100-104 (1996).
M. Okuno et al., "Retinoids Exacerbate Rat Liver Fibrosis by Inducing the Activation of latent TGF-β in Liver Stellate Cells," Hepatology (Philadelphia), vol. 26, No. 4, pp. 913-921 (1997).
Di Bisceglie A.M. et al., "Hepatocellular Carcinoma," Hepatology, vol. 28, No. 4, pp. 1161-1165 (1998).
Ishiwari, K., "The Effects of a Synthetic Retinoid on Phenotypic Expression of Cultured Mesangial Cells," Kyoto-furitsu Ika Daigaku Zasshi, vol. 106, No. 3, pp. 273-283 (1997).
Yasutoshi Muto, et al., "Prevention of Second Primary Tumors by an Acyclic Retinoid in Patients with Hepatocellular Carcinoma" New Eng. J. Med., vol. 340, No. 13, pp. 1046-1047 (1999).

(Continued)

*Primary Examiner* — Kevin E Weddington
(74) *Attorney, Agent, or Firm* — Greenblum & Bernstein, P.L.C.

(57) ABSTRACT

Activators of peroxisome proliferator-activated receptors comprising a polyprenyl compound, preferably (2E,4E,6E,10E)-3,7,11,15-tetramethyl-2,4,6,10,14-hexadecapentaenoic acid, as an active ingredient, and medicaments for preventive and/or therapeutic treatment of hyperlipidemia, non-insulin dependent diabetes mellitus or the like comprising a polyprenyl compound as an active ingredient.

3 Claims, 1 Drawing Sheet

OTHER PUBLICATIONS

K. Tago et al., "A Practical Total Synthesis of Plaunotol via Highly Z-selective Wittig Olefination of α-acetal ketones," J. Chem. Soc. Perkin Trans. 1, pp. 2073-2078 (2000).
W.C. Still et al., "Direct Synthesis of Z-Unsaturated Esters. A Useful Modification of the Horner-Emmons Olefination," Tetrahedron Letters, vol. 24, No. 41, pp. 4405-4408 (1983).
T. Kajiwara et al., "Stereoselective Synthesis of Ectocarpene and Its Antipode via Microbiological Asymmetric Hydrolysis," Agric. Biol. Chem., vol. 45, pp. 1461-1466 (1981).
Chinese Journal of Applied Chemistry, vol. 5, 1988, pp. 70-71.
R. Boden, "A Mild Method for Preparing trans-Alkenes; Crown Ether Catalysis of the Wittig Reaction," Synthesis, p. 784 (1975).
G. Bellucci et al., "Crown Ether Catalyzed Stereospecific Synthesis of Z- and E-Stilbenes by Wittig Reaction in a Solid-Liquid Two-Phases System," Tetrahedron Letters, vol. 37, No. 24, pp. 4225-4228 (1996).
M. Mikolajczyk et al., "Synthesis of α,β-Unsaturated Sulphides, Sulphoxides, and Sulphones by the Horner-Wittig Reaction in Two-Phase System Catalysed by Quaternary Ammonium Salts and Crown Ethers," Synthesis, pp. 278-280 (1975).
Izv. Akad. Nauk SSSR, Khim., 1990, pp. 2544-2550.
Izv. Akad. Nauk SSSR, Khim., 1988, pp. 2382-2385.
Izv. Akad. Nauk SSSR, Khim., 1988, pp. 2377-2382.
R.N. Gedye et al., "The Stereochemistry of the Wittig Reactions of Allylic Phosphroranes and Phosponate Esters with Aldehydes," Can. J. Chem., vol. 55, pp. 1218-1228 (1977).
K. Ashizawa et al., "The Crystal Structure of 3,7,11,15-Tetramethyl-2,4,6,10,14—All Trans-Hexadecapentaenoic Acid (E-5166)," Chem. Pharm. Bull., vol. 33, No. 7, pp. 3062-3064 (1985).
Reaven, G.M., Diabetes, vol. 37, pp. 1595-1607 (1988).
Issemann, I., et al., Nature, vol. 347, pp. 645-650, 1990.
Lehmann, J.M., et al., J. Biol. Chem. vol. 270, pp. 12953-12956, 1995.
Saltiel, A.R., et al., Diabetes, vol. 45, pp. 1661-1669, 1996.
Rinshu Iyaku., et al., vol. 14, pp. 461-466, 1998.
Muto, Y., et al., N. Eng. J. Med., 334, pp. 1561-1567, 1996.
Davis, J.B., et al., J. Chem. Soc (C), pp. 2154-2165, 1966.
Ellinghaus, P., et al., J. Biol. Chem., vol. 274, No. 5, pp. 2766-2772 (1999).
Kliewer, S.A., et al., Proc. Natl. Acad. Sci. U.S.A., vol. 94, No. 9, pp. 4318-4323 (1997).
Göttlicher, M., et al., Biochem. Pharmacol., vol. 46, No. 12, pp. 2177-2184 (1993).
Issemann, I., et al., J. Mol. Endocrinol., vol. 11, No. 1, pp. 37-47 (1993).
Remngton: The Science and Practice of Pharmacy, Mack Publishing Co., Nineteenth Edition, vol. 1(1995), Chapter 48, "The Introduction of New Drugs", pp. 795-808.
Http://www.truestarthealth.com /Notes/1028005.htm (2007) High Cholesterol.
English Language Abstract of JP 56-140949 corresponding to JP Appln. No. 63-32058, published Jun. 28, 1998.
English language Abstract of JP 10-167960, published Jun. 23, 1998.
English language Abstract of JP 54-046821, published Apr. 13, 1979.
English language Abstract of JP 55-22645, published Feb. 18, 1980.
English language Abstract of JP 58-109415, published Jun. 29, 1983.
English language Abstract of JP62-77317, published Apr. 9, 1987.
English language Abstract of JP63-166824, published Jul. 11, 1988.
English Langune Abstract of JP 57-106638 corresponding to JP Appln. No. 63-34855, published Jul. 12, 1988.
Shibata et al. (Shibata), British Journal of Pharmacology (2000) 130, 495-504.
Takamura et al. (Takamura), Diabetes Research and Clinical Practice 44 (1999) 107-114.
Yamada et al., Mol. Carcinog., 1994, vol. 10, No. 3, p. 151-158.
Nakamura et al., Biochem. Biophys. Res. Commu., 1995, vol. 207, No. 1, p. 382-388.
Issemann et al., J. Mol. Endocrinol., 1993, Vo.11, No. 1, p. 37-47.
Zhu et al., Biochem. Biophys. Res. Commu., 1998., vol. 25 1, No. 3, p. 842-848.
Valmascda et al., Mol. Cell. Endocrinol., 1999, vol. 154, No. 1-2, p. 101-109.
Japanese Office Action, dated May 17, 2011 issued in connection with JP 2001-577953.

\* cited by examiner

ACTIVATORS OF PEROXISOME PROLIFERATOR-ACTIVATED RECEPTORS

CROSS-REFERENCE TO RELATED APPLICATIONS

The present application is a continuation of application Ser. No. 11/845,684, filed Aug. 27, 2007, which is a divisional of application Ser. No. 11/272,864, filed Nov. 15, 2005, which is a continuation of application Ser. No. 10/257,391, the entire disclosures of which applications are expressly incorporated by reference herein, which is a U.S. National Phase of International Application PCT/JP01/03442, filed Apr. 23, 2001, claiming priority of Japanese Patent Application 2000-122974, filed Apr. 24, 2000.

TECHNICAL FIELD

The present invention relates to an activator of peroxisome proliferator-activated receptors (abbreviated sometimes as "PPAR" in the specification).

BACKGROUND ART

Patients with hyperlipidemia or diabetes are estimated currently as 10 million or more in total in our country, and the number has been steadily increasing. Many of patients with diabetes suffer from non-insulin dependent diabetes mellitus, which is characterized by a pathological condition presenting hyperglycemia is resistant to the insulin action. Further, symptoms such as hyperinsulinemia, hypo HDL cholesterolemia, hypertension, and obesity most frequently occur with hyperlipidemia and diabetes, which raises clinical problems. In recent years, such pathological conditions presenting these multiple symptoms are referred to as Syndrome X, and considered as one of severe diseases (Reference: Diabetes, 37, 1595-1607 (1988)).

As medicaments for therapeutic treatment of these diseases, clofibrate derivatives including clofibrate as a typical example, thiazolidine derivatives including pioglitazone and troglitazone as typical examples and the like have been used. The clofibrate derivatives have an activating action on PPAR α (Reference: Nature, 347, 645-650 (1990)) and are considered to improve lipid metabolism through the aid of fatty acid β-oxidation enzymes in the liver. The thiazolidine derivatives have an activating action on PPAR γ (Reference: J. Biol. Chem., 270, 112953-112956 (1995)) and are considered to ameliorate insulin resistance and thereby lower a blood sugar level (Reference: Diabetes, 45, 1661-1669 (1996)).

However, PPAR agonists are reported to generally have adverse effects such as liver function failure, and accordingly, a patient with liver function failure. contraindicates the use of troglitazone, one of the PPAR γ agonists (Reference: Rinsho Iyaku, 14, 461-466 (1998)), and the sale of said drug was currently discontinued.

As described above, medicaments having the PPAR activation activity are useful as therapeutic agents for hyperlipidemia and diabetes. However, since they have various adverse effects, medicaments activating PPAR have been desired which have reduced adverse effects.

(2E,4E,6E,10E)-3,7,11,15-Tetramethyl-2,4,6,10,14-hexadecapentaenoic acid (Development Code: "NIK-333"), one of polyprenyl compounds, is known to have affinities for retinoic acid binding proteins and retinoic acid receptors and to have actions of inducing differentiation and apoptosis in hepatocellular carcinoma. Clinically, NIK-333 significantly inhibited recurrence of hepatoma after radical treatment of hepatoma by long-term administration for one-year, and thus its action of suppressing recurrence of hepatoma was suggested. Further, NIK-333 is proved to be a safe drug, because almost no liver function failure or almost no other adverse effect, generally accompanied with retinoids, was observed during the administration (Reference: N. Eng. J. Med., 334, 1561-1567 (1996)).

However, it his not been known that a polyprenyl compound activates PPAR.

DISCLOSURE OF THE INVENTION

Accordingly, an object of the present invention is to provide PPAR activators with reduced adverse effects.

The inventors of the present invention conducted various researches to find PPAR activators. As a result, they found that polyprenyl compounds induced expression of PPAR α and PPAR γ mRNAs and that the compounds had ligand activity for PPAR α. On the basis of these results, they found that the polyprenyl compounds activated PPAR, and as a result of further researches, they achieved the present invention.

The present invention thus provides an activator of peroxisome proliferator-activated receptor (PPAR) comprising a polyprenyl compound as an active ingredient. The present invention further provides a medicament for preventive and/or therapeutic treatment of hyperlipidemia or non-insulin dependent diabetes mellitus which comprises a polyprenyl compound as an active ingredient.

From another aspect, the present invention provides a use of a polyprenyl compound for manufacture of the aforementioned medicament; a methods for activating peroxisome proliferator-activated receptor (PPAR) in a mammal including human, which comprise a step of administering an effective amount of a polyprenyl compound to a mammal including human; and a method for preventive and/or therapeutic treatment of hyperlipidemia or non-insulin dependent diabetes mellitus, which comprise the step of administering a preventively and/or therapeutically effective amount of a polyprenyl compound to a mammal including human in need of such preventive and/or therapeutic treatment.

BEST MODE FOR CARRYING OUT THE INVENTION

Figure 1:
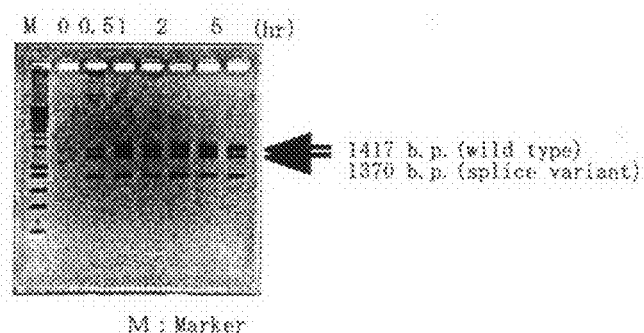
FIG. 1 shows expression of PPAR α mRNA in cells treated with NIK-333 (wild type, splice variant).

The whole disclosures of Japanese Patent Application No. 2000-122974 (filed on Apr. 24, 2000) are incorporated by reference in disclosures in the specification.

Among polyprenyl compounds used in the present invention, a particularly preferred compound includes (2E,4E,6E,10E)-3,7,11,15-tetramethyl-2,4,6,10,14-hexadecapentaenoic acid (NIK-333). Other examples of the polyprenyl compounds include conjugated polyprenylcarboxylic acids (polyprenoic acids) such as 3,7,11,15-tetramethyl-2,4,6,10,14-hexadecapentaenoic acid and esters thereof described in Japanese Patent Publication (Kokoku) No. 63-34855 and the like.

The polyprenyl compounds used in the present invention can be synthesized by a known method (Japanese Patent Publication (Kokoku) No. 63-32058, J. Chem. Soc. (C), 2154 (1966)).

When the PPAR activator of the present invention or the medicament of the present invention for preventive and/or therapeutic treatment of hyperlipidemia or non-insulin dependent diabetes mellitus based on the PPAR activating action is used, a pharmaceutical composition comprising the polyprenyl compound can be generally prepared and administered via an appropriate administration route, i.e., oral or parenteral route. Examples of forms of the pharmaceutical composition suitable for oral administration include tablets, granules, capsules, soft capsules, pills, powders, solutions and the like. Examples of forms of the pharmaceutical composition suitable for parenteral administration include injections, suppositories and the like. These pharmaceutical compositions can be prepared by an ordinary method using a polyprenyl compound or a pharmacologically acceptable salt thereof and one or more kinds of ordinary pharmaceutically acceptable pharmaceutical carriers. Two or more kinds of polyprenyl compounds as active ingredients may be used in combination.

For example, for the medicaments suitable for oral administration, desired pharmaceutical compositions can be prepared by using, as pharmaceutical carriers, excipients such as lactose, glucose, corn starch, and sucrose, disintegrants such as carboxymethylcellulose calcium, and hydroxypropylcellulose, lubricants such as calcium stearate, magnesium stearate, talc, polyethylene glycol, and hydrogenated oil, binders such as hydroxypropylcellulose, hydroxypropylmethylcellulose, carboxymethylcellulose, polyvinyl alcohol, gelatin, and gum arabic, moistening agents such as glycerine and ethylene glycol, as well as surfactants, flavoring agents and the like as optionally required.

For the medicaments suitable for parenteral administration, diluents such as water, ethanol, glycerine, propylene glycol, polyethylene glycol, vegetable oil, agar, and gum tragacanth may be used as pharmaceutical carriers, as well as solubilizing agents, suspending agents, emulsifiers, buffers, isotonic agents, preservatives, soothing agents and the like may be used as optionally required.

The medicament of the present invention can be applied to diseases that are therapeutically and/or preventively treatable by PPAR activation, and the medicament can be used for mammals including human. Examples of PPAR that can be activated by the medicament of the present invention include PPAR α or PPAR γ as preferred targets. Examples of conditions to which the medicaments of the present invention can be preferably applied include non-insulin dependent diabetes mellitus and hyperlipidemia, as well as complications of these diseases, for example, hyperinsulinemia, hypo HDL cholesterolemia, hypertension, obesity and the like.

When the PPAR activator of the present invention or the medicament of the present invention for preventive and/or therapeutic treatment of hyperlipidemia or non-insulin dependent diabetes mellitus based on the PPAR activating action is used, doses are not particularly limited. For example, 1 to 2,000 mg, preferably 20 and 800 mg, can be administered per day for an adult for oral administration. For parenteral administration, doses may be in the range of 1 to 1,000 mg, preferably in the range of 10 to 100 mg. Desired preventive and/or therapeutic effects can be expected by administration of the aforementioned dose once to 3 times a day.

EXAMPLES

The present invention will be explained more specifically with reference to the following examples. However, the scope of the present invention is not limited to these examples.

Example 1

Expression of PPAR α and PPAR γ mRNA in human cell line

Caco-2 cells (derived from colon cancer) as a human cell line were cultured at 37° C. in RPMI-1640 medium containing 10% fetal calf serum in the presence of 5% $CO_2$. The medium was then replaced with serum-free RPMI-1640 medium and the cells were cultured for 48 hours. In order to examine the effect of NIK-333, a solution of NIK-333 in ethanol was added at a final concentration of 10 μM. At 0, 0.5, 1, 2 and 5 hours after the addition, RNA was extracted to observe. mRNA for PPAR α, PPAR γ1 and PPAR γ2 by the RT-PCR method.

Figure 2:
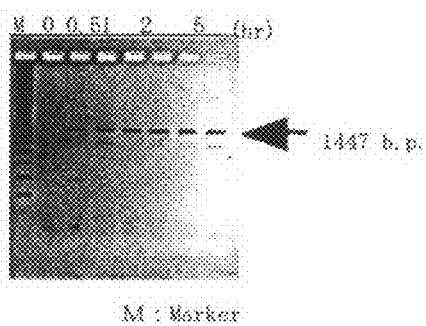
FIG. 2 shows expression of PPAR γ1 mRNA in cells treated with NIK-333.

As a result, expression of PPAR α mRNA was observed from 0.5 hour after the addition of NIK-333 (FIG. 1). Further, expression of PPAR γ1 mRNA was also observed from 0.5 hour after the addition of NIK-333 (FIG. 2), whilst expression of PPAR γ2 mRNA was not observed.

Example 2

Ligand activity for PPAR α

COS-7 cells, a cell line derived from monkey kidney, were cultured at 37° C. in DMEM medium containing 10% fetal calf serum in the presence of 5% $CO_2$. Then, expression vectors of RXR α (retinoic acid X receptor α) and PPAR α, and a reporter vector incorporated with PPRE (peroxisome proliferator-responsive element) as a PPAR-responsive element were cotransfected into the cells, and the cells were cultured for 24 hours. In order to examine the effect of NIK-333, a solution of NIK-333 or Wy-14643 (selective agonist of PPAR α) in ethanol was added at a final concentration of 10 μM. After cultivation for 24 hours, the activity of firefly luciferase was measured. The measured values were represented as values standardized by using the renilla luciferase activity.

Figure 3:
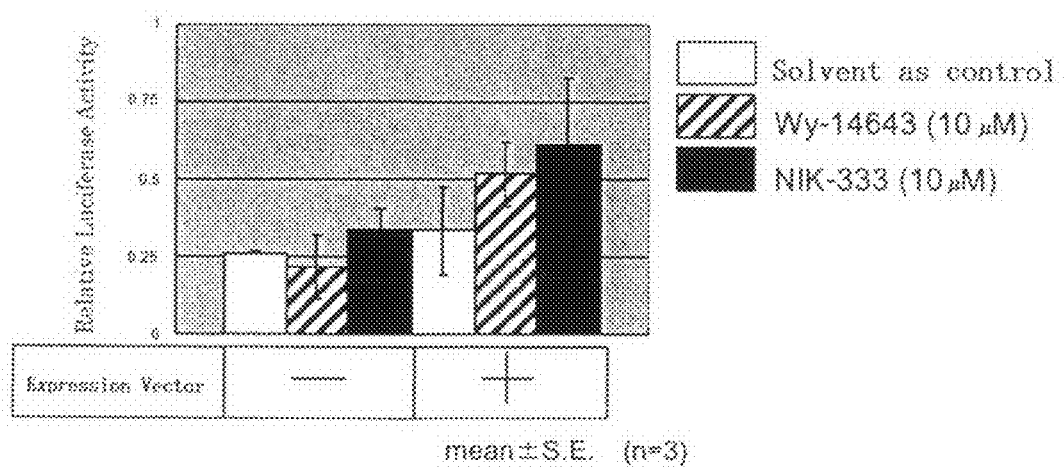
FIG. 3 shows ligand activity of NIK-333 or Wy-14643 for PPAR α with introduction of a PPAR α expression vector (+) and without introduction of the same (−).

As shown in FIG. 3, NIK-333 and Wy-14643 failed to increase the luciferase activity when the PPAR α expression vector was not introduced (−), whereas they increased the luciferase activity only when the PPAR α expression vector was introduced (+). NIK-333 exhibited increasing action of ligand activity almost equivalent to the action of Wy-14643.

INDUSTRIAL APPLICABILITY

Polyprenyl compounds induce expression of PPAR α and PPAR γ and also have ligand activity for PPAR α. Therefore, these compounds have a PPAR activation action and are useful for preventive and/or therapeutic treatment of hyperlipidemia or non-insulin dependent diabetes mellitus.

What is claimed is:

1. A method of prophylaxis of non-insulin dependent diabetes mellitus, wherein the method comprises administering a prophylactically effective amount of at least one polyprenyl compound to a patient in need thereof, the at least one polyprenyl compound comprising 3,7,11,15-tetramethyl-2,4,6,10,14-hexadecapentaenoic acid.

2. The method of claim 1, wherein the at least one polyprenyl compound comprises (2E,4E,6E,10E)-3,7,11,15-tetramethyl-2,4,6,10,14-hexadecapentaenoic acid.

3. The method of claim 1, wherein the at least one polyprenyl compound is in an orally administrable form.

* * * * *